(12) United States Patent
Leporq et al.

(10) Patent No.: US 10,251,599 B2
(45) Date of Patent: Apr. 9, 2019

(54) METHOD FOR POST-PROCESSING MAGNETIC RESONANCE IMAGING IMAGES IN A CLINICAL CONTEXT

(71) Applicants: INSTITUT NATIONAL DE LA SANTE ET DE LA RECHERCHE MEDICALE (INSERM), Paris (FR); Universite Paris Diderot—Paris 7, Paris (FR)

(72) Inventors: Benjamin Leporq, Clichy (FR); Simon Lambert, Clichy (FR); Bernar Van Beers, Clichy (FR)

(73) Assignees: INSERM(INSTITUT NATIONAL DE LA SANTÉET DE LA RECHERCHE MÉDICALE), Paris (FR); UNIVERSITE PARIS DIDEROT-PARIS 7, Paris (FR)

( * ) Notice: Subject to any disclaimer, the term of this patent is extended or adjusted under 35 U.S.C. 154(b) by 1003 days.

(21) Appl. No.: 14/695,723

(22) Filed: Apr. 24, 2015

(65) Prior Publication Data

US 2016/0310035 A1 Oct. 27, 2016

(51) Int. Cl.
*A61B 5/00* (2006.01)
*A61B 5/055* (2006.01)
(Continued)

(52) U.S. Cl.
CPC ............ *A61B 5/4872* (2013.01); *A61B 5/055* (2013.01); *A61B 5/748* (2013.01); *G01R 33/243* (2013.01); *G01R 33/4828* (2013.01); *G01R 33/50* (2013.01); *G01R 33/5608* (2013.01); *G01R 33/5615* (2013.01); *G01R 33/5616* (2013.01); *G01R 33/5618* (2013.01); *A61B 2576/00* (2013.01)

(58) Field of Classification Search
CPC combination set(s) only.
See application file for complete search history.

(56) References Cited

U.S. PATENT DOCUMENTS

2004/0032977 A1* 2/2004 Blezek ............... G01R 33/4828
382/128
2011/0044524 A1* 2/2011 Wang ..................... G01R 33/54
382/131

(Continued)

FOREIGN PATENT DOCUMENTS

WO 2009/129138 A1 10/2009
WO 2012/061839 A2 5/2012

OTHER PUBLICATIONS

B. Leporq et al., "Quantification of triglyceride fatty acid composition in the fatty liver, subcutaneous and visceral adipose tissues with 3.0T MRI", Joint Annual Meeting ISMRM-ESMRMB, May 10, 2014, Poster.

(Continued)

*Primary Examiner* — Tsung Yin Tsai
(74) *Attorney, Agent, or Firm* — W&C IP

(57) ABSTRACT

A method for post-processing images of a region of interest in a subject, the images being acquired with a magnetic resonance imaging technique, the method for post-processing comprising at least the step of:
unwrapping the phase of each image,
extracting a real signal over echo time for at least one pixel of the unwrapped images, and
calculating fat characterization parameters by using a fitting technique applied on a model,
the model being a function which associates to a plurality of parameters each extracted real signal, the plurality of parameters comprising at least two fat characterization parameters and at least one parameter obtained by a measurement,
the fitting technique being a non-linear least-square fitting technique using pseudo-random initial conditions.

17 Claims, 9 Drawing Sheets

(51) Int. Cl.
  *G01R 33/24* (2006.01)
  *G01R 33/48* (2006.01)
  *G01R 33/50* (2006.01)
  *G01R 33/561* (2006.01)
  *G01R 33/56* (2006.01)

(56) References Cited

U.S. PATENT DOCUMENTS

2012/0268121 A1* 10/2012 Hernando ............... G01R 33/50
　　　　　　　　　　　　　　　　　　　　　　324/309
2016/0041247 A1* 2/2016 Feiweier ................. A61B 5/055
　　　　　　　　　　　　　　　　　　　　　　324/309

OTHER PUBLICATIONS

B. Leporq et al., "Quantification of triglyceride fatty acid composition in the fatty liver, subcutaneous and visceral adipose tissues with 3.0T MRI", Apr. 25, 2014, Abstract.

Berglund et al., "Model Based Mapping of Fat Unsaturation and Chain Length by Chemical Shift Imaging—Phantom Validation and In Vivo Feasibility", Magnetic Resonance in Medicine, 2012, vol. 68, pages.

Peterson et al., "Simultaneous Quantification of Fat Content and Fatty Acid Composition Using MR Imaging", Magnetic Resonance in Medicine, 2013, vol. 29, pp. 688-697.

Bydder et al., "Mapping the double bonds in triglycerides", Magnetic Resonance Imaging, 2011, vol. 29, pp. 1041-1046.

Hamilton et al., "In vivo characterization of the liver fat 1H MR spectrum", NMR Biomed, 2010, Web.

Peterson et al., "Fat Quantification Using Multiecho Sequences with Bipolar Gradients: Investigation of Accuracy and Noise Performance", Magnetic Resonance in Medicine, 2014, vol. 71, pp. 219-229.

Leporq et al., "Quantification of the triglyceride fatty acid composition with 3.0T MRI", NMR Biomed, 2014, Web.

* cited by examiner

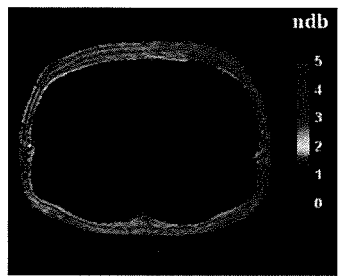
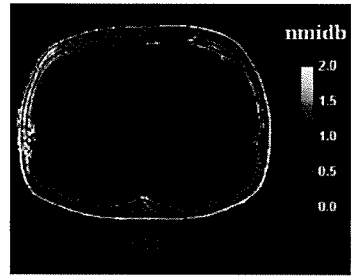
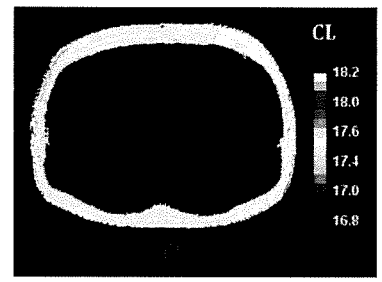
FIG.28　　　　　FIG.29　　　　　FIG.30
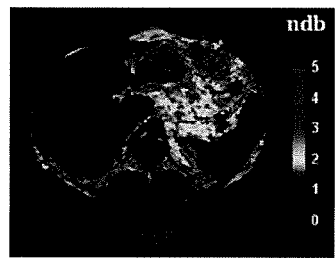
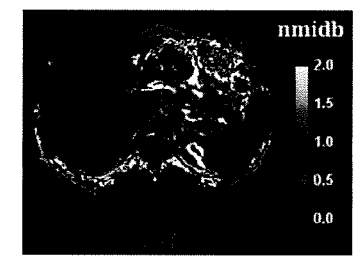
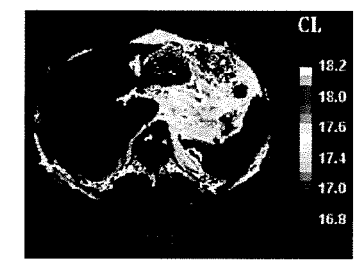
FIG.31　　　　　FIG.32　　　　　FIG.33
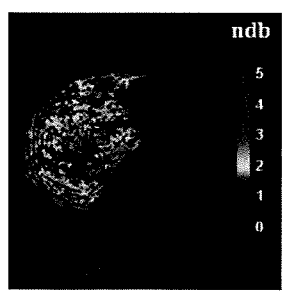
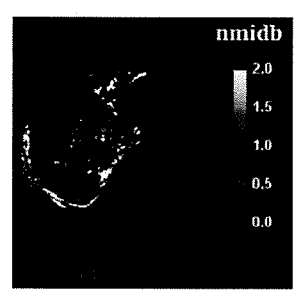
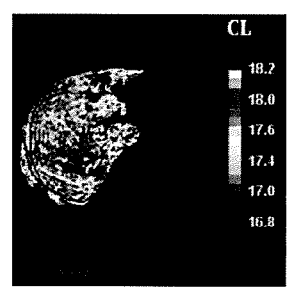
FIG.34　　　　　FIG.35　　　　　FIG.36

METHOD FOR POST-PROCESSING MAGNETIC RESONANCE IMAGING IMAGES IN A CLINICAL CONTEXT

TECHNICAL FIELD OF THE INVENTION

The invention relates to a method for post-processing images of a region of interest in a subject. The invention also concerns a method for predicting that a subject is at risk of suffering from an obesity related disease. The invention also relates to a method for diagnosing an obesity related disease. The invention also concerns a method for monitoring the responsiveness of a subject suffering from an obesity related disease to a treatment useful for said disease. The invention also relates to a method for screening a probiotic, a prebiotic, a chemical compound or a biological compound suitable for obtaining a treatment useful for an obesity related disease. The invention also concerns a method for monitoring the proportion of unsaturated fatty acids and proportion of saturated fatty acids in a region of interest in a subject. The invention also relates to the associated device, computer program products and information supports.

BACKGROUND OF THE INVENTION

Suboptimal diet is the single leading modifiable cause of poor health in the world. High fat intake causes obesity and increases the risk of cardiovascular diseases, type-2 diabetes mellitus, and cancer. The metabolic risks are related to ectopic fat deposition in the abdomen and the liver and are influenced by the intake of saturated fatty acids (SFA).

Moreover, the protective effects of replacing SFA with polyunsaturated fatty acids (PUFA) have been demonstrated for coronary heart disease and for some cancers, especially when omega-3 PUFA are administered.

These points underscore the fact that obesity related diseases are caused not only by the total amount of fat, but also by visceral fat distribution and fatty acid composition.

Therefore, it is desirable to develop non-invasive methods to quantify the amount and composition of abdominal fat.

It is known from document WO 2012/061839 A2 techniques, apparatus and systems are described for using parameters including chain length, number of double bonds and number of double-double bonds of a complex, magnetic resonance imaging (MRI)-generated fat spectrum to determine the composition and properties of fat and to perform various diagnostic functions. In one aspect, a method using magnetic resonance imaging to characterize fat includes acquiring a magnetic resonance (MR) image that includes MR data from a target, determining fat characterization parameters based on the acquired MR data, and using the determined fat characterization parameters to produce a relationship between regions of fat and/or water in the MR image.

However, such technique does not provide with enough accuracy in the context of clinical magnetic resonance imaging systems.

SUMMARY OF THE INVENTION

The invention aims at providing a method which can provide accurate results, notably in the context of clinical magnetic resonance imaging systems.

To this end, the invention concerns a method for post-processing images of a region of interest in a subject, the images being acquired with a magnetic resonance imaging technique, the magnetic resonance imaging technique involving successive echoes of a multiple-gradient echo sequence, each image associating to each pixel of the image the amplitude of the measured signal in the magnetic resonance imaging technique and the phase of the measured signal in the magnetic resonance imaging technique, the method for post-processing comprising at least the step of:
  unwrapping the phase of each image, to obtain unwrapped images,
  extracting a real signal over echo time for at least one pixel of the unwrapped images, to obtain at least one extracted real signal,
  calculating fat characterization parameters by using a fitting technique applied on a model,
  the model being a function which associates to a plurality of parameters each extracted real signal, the plurality of parameters comprising at least two fat characterization parameters and at least one parameter obtained by a measurement,
  the fitting technique being a non-linear least-square fitting technique using pseudo-random initial conditions.

Thanks to the invention, images taken the context of clinical magnetic resonance imaging systems may be post-processed to calculate fat characterization parameters with a good accuracy.

According to further aspects of the invention which are advantageous but not compulsory, the method for post-processing images might incorporate one or several of the following features, taken in any technically admissible combination:
  the fat characterization parameters are chosen in the group consisting of the number of double bounds, the number of methylene-interrupted double bounds and the chain length.
  the method for post-processing images further comprises the step of:
    measuring the field inhomogeneity in the magnetic field used in the magnetic resonance imaging technique, and
    measuring the transversal relaxivity rate,
  the parameters obtained by a measurement the field inhomogeneity in the magnetic field used in the magnetic resonance imaging technique and the transversal relaxivity rate.
  the calculating step comprises several sub-steps of calculating by using the model in which at least one parameters is fixed.
  the method for post-processing images further comprises the step of quantifying the proportion of unsaturated fatty acids and proportion of saturated fatty acids in the region of interest in the subject based on the calculated fat characterization parameters.
  the quantifying step comprises determining the fatty acid composition based on the calculated fat characterization parameters.

It is also proposed a method for predicting that a subject is at risk of suffering from an obesity related disease, the method for predicting at least comprising the step of:
  carrying out the steps of the method for post-processing images of the subject as previously described, to obtain fat characterization parameters, and
  predicting that the subject is at risk of suffering from the obesity related disease based on the fat characterization parameters.

It also concerns a method for diagnosing an obesity related disease, the method for diagnosing at least comprising the step of:

carrying out the steps of the method for post-processing images of the subject as previously described, to obtain fat characterization parameters, and diagnosing the obesity related disease based on the fat characterization parameters.

It is also proposed a method for monitoring the responsiveness of a subject suffering from an obesity related disease to a treatment useful for said disease, the method for monitoring the responsiveness comprising:

carrying out the steps of the method for post-processing images of the subject as previously described, to obtain fat characterization parameters before the treatment, carrying out the steps of the method for post-processing images of the subject as previously described, to obtain fat characterization parameters during or after the treatment, and comparing the fat characterization parameters before the treatment with the fat characterization parameters during or after the treatment, a difference between said fat characterization parameters being indicative that the treatment is effective.

It also concerns a method for screening a probiotic, a prebiotic, a chemical compound or a biological compound suitable for obtaining a treatment useful for an obesity related disease using the method for monitoring the responsiveness of a subject as previously described.

It is also proposed a method for monitoring the proportion of unsaturated fatty acids and proportion of saturated fatty acids in a region of interest in a subject, the method for monitoring at least comprising the step of:

imaging the region of interest in the subject by using an magnetic resonance imaging technique, the magnetic resonance imaging technique involving successive echoes of a multiple-gradient echo sequence, to obtain images, carrying out the steps of the method for post-processing the obtained images as previously described, to obtain fat characterization parameters, and quantifying the proportion of unsaturated fatty acids and proportion of saturated fatty acids in the region of interest in the subject based on the calculated fat characterization parameters.

According to a specific embodiment, the magnetic resonance imaging technique involves using a magnetic field value comprised between 1.0 T and 11.7 T.

It also concerns a computer program product comprising instructions for carrying out the steps of a method for post-processing images as previously described when said computer program product is executed on a suitable computer device.

It is also proposed a computer program product comprising instructions for carrying out the steps of a method for method for predicting as previously described when said computer program product is executed on a suitable computer device.

It also concerns a computer program product comprising instructions for carrying out the steps of a method for diagnosing an obesity related disease as previously described when said computer program product is executed on a suitable computer device.

It is also proposed a device for monitoring the proportion of unsaturated fatty acids and proportion of saturated fatty acids in a region of interest in a subject, the device comprising:

a magnetic resonance imaging system adapted to image the region of interest in the subject by using a magnetic resonance imaging technique, the magnetic resonance imaging technique involving successive echoes of a multiple-gradient echo sequence to obtain images and a controller adapted to:

receive the obtained images of the region of interest from the magnetic resonance imaging system, each image associating to each pixel of the image the amplitude of the measured signal in the magnetic resonance imaging technique and the phase of the measured signal in the magnetic resonance imaging technique, unwrap the phase of each image, to obtain unwrapped images, extract a real signal over echo time for at least one pixel of the unwrapped images, to obtain at least one extracted real signal, calculate fat characterization parameters by using a fitting technique applied on a model, the model being a function which associates to a plurality of parameters each extracted real signal, the plurality of parameters comprising at least two fat characterization parameters and at least one parameter obtained by a measurement, the fitting technique being a non-linear least-square fitting technique using pseudo-random initial conditions, and quantify the proportion of unsaturated fatty acids and proportion of saturated fatty acids in the region of interest in the subject based on the calculated fat characterization parameters.

According to further aspects of the invention which are advantageous but not compulsory, the device for monitoring the proportion of unsaturated fatty acids and proportion of saturated fatty acids in a region of interest in a subject might incorporate one or several of the following features, taken in any technically admissible combination:

the magnetic resonance imaging system is adapted to apply a magnetic field whose magnetic field value comprised between 1.0 T and 11.7 T.

the magnetic resonance imaging system is adapted to apply a magnetic field whose magnetic field value comprised between 1.5 T and 3.0 T.

BRIEF DESCRIPTION OF THE DRAWINGS

The invention will be better understood on the basis of the following description which is given in correspondence with the annexed figures and as an illustrative example, without restricting the object of the invention. In the annexed figures.

Nevertheless, for fatty acid composition range of in vivo and vegetable oil triglycerides, the error is close to 10%.

FIGS. 7 to 12 are phantom parametric maps of PDFF (%), T2* (ms), $\Delta B_0$ field map (Hz), ndb, nmidb and CL. These maps illustrate the difference in fatty acid composition between oils. The number of double bounds ndb and the number of methylene interrupted double bounds nmidb maps highlight the difference between walnut oil mainly composed of polyunsaturated fatty acids and olive oil mainly composed of monounsaturated fatty acids.

Figure 13:
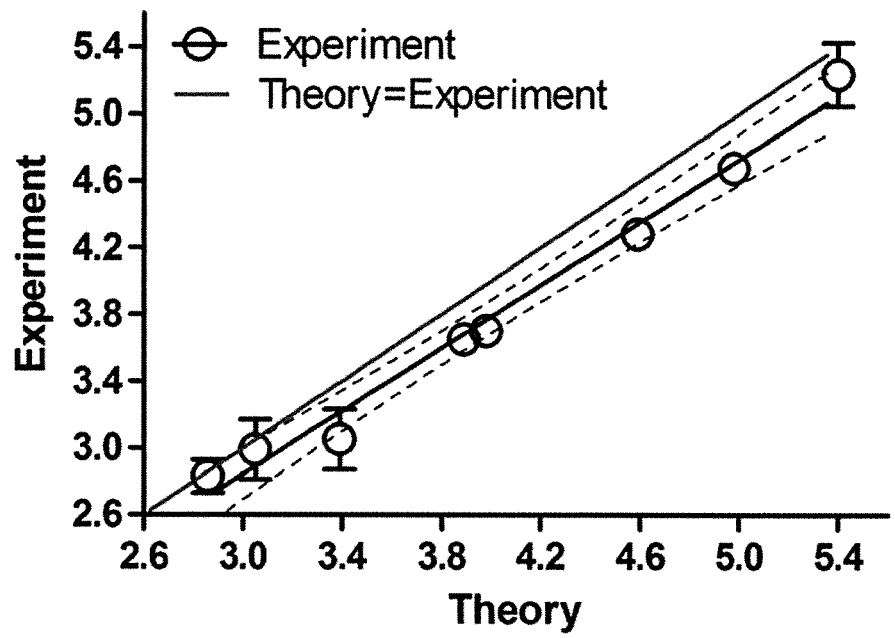
Figure 14:
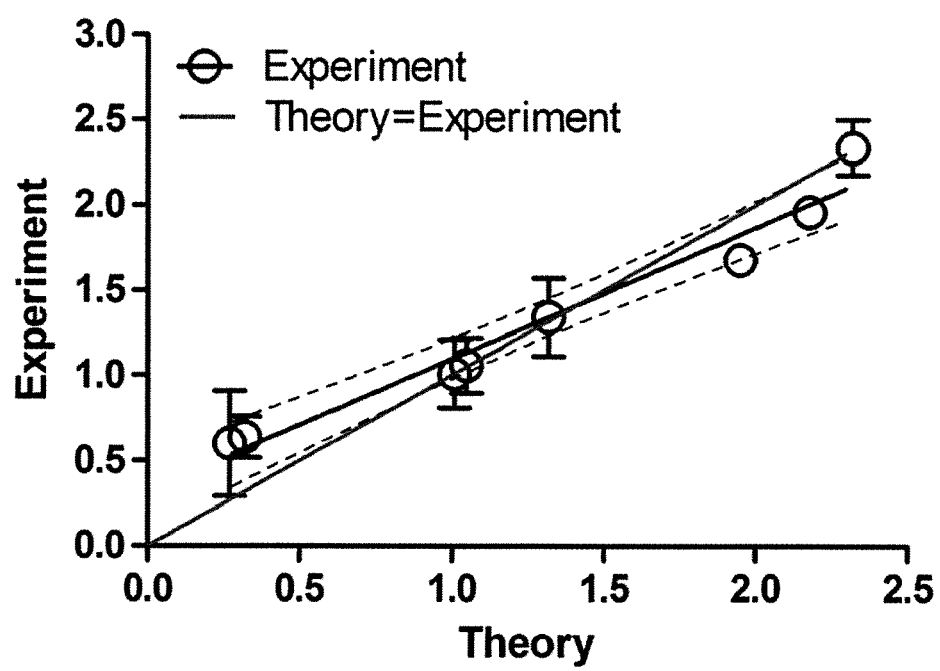
Figure 15:
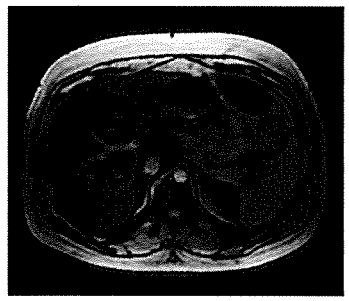
Figure 16:
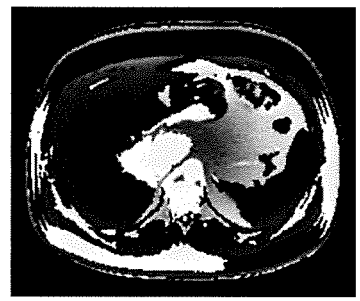
Figure 17:
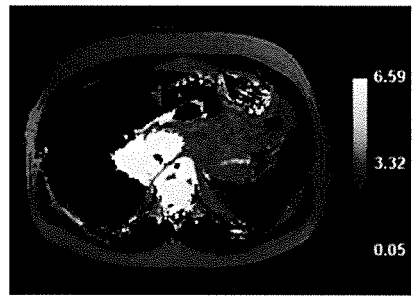
Figure 18:
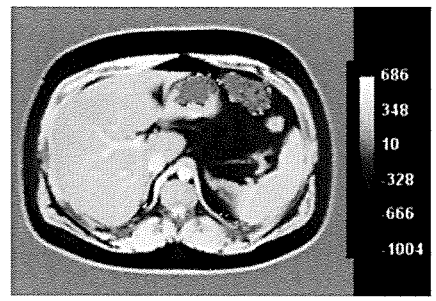
Figure 19:
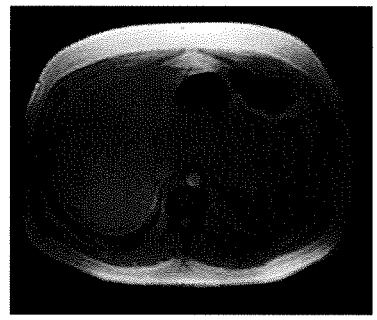
Figure 20:
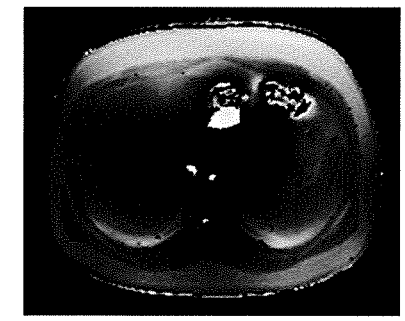
Figure 21:
Figure 22:
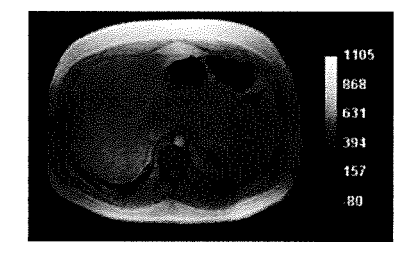
Figure 23:
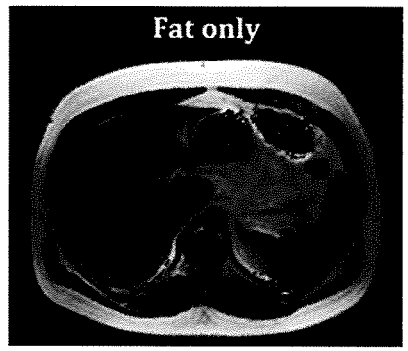
Figure 24:
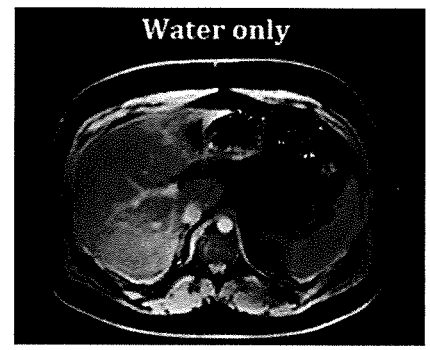
Figure 25:
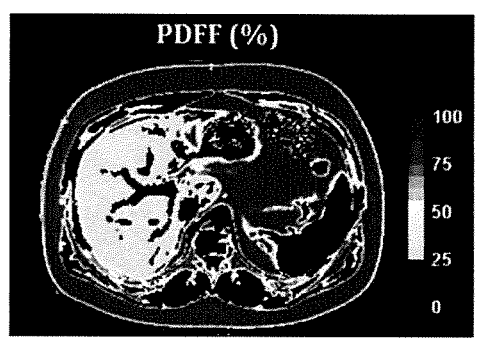
Figure 26:
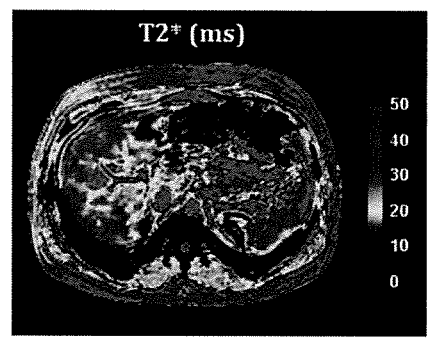
Figure 27:
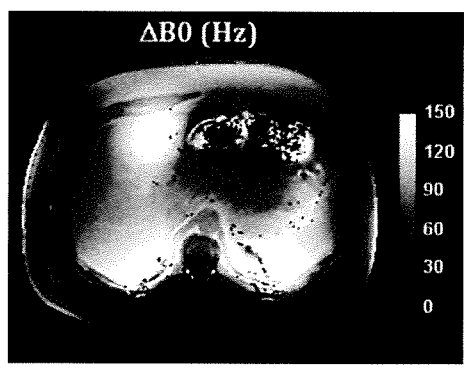

FIGS. 13 and 14 illustrate linear regression between theoretical and experimental number of double bounds ndb (FIG. 13) and number of methylene interrupted double bounds nmidb (FIG. 14) quantified with the experimental method and with theoretical values obtained from mass composition of each oil.

FIGS. 15 to 18 respectively represent magnitude and native phase images acquired in an obese subject; phase-corrected image taking into account wrap, zero- and first-order phase; and real part images presented for the first echo (1.15 ms);

FIGS. 19 to 22 respectively represent magnitude and native phase images acquired in an obese subject; phase-corrected image taking into account wrap, zero- and first-order phase; and real part images presented for the second echo (2.3 ms);

FIGS. 23 to 27 are fat and water only images and parametric maps (PDFF, T2*, $B_0$ field) processed with the experimental method from an obese subject;

FIGS. 28 to 30 are parametric maps of the number of double bounds ndb, the number of methylene interrupted double bounds nmidb and the chain length CL in SAT performed in an obese subject. The maps are derived from native parametric maps after the application of a four-cluster mask to segment SAT;

FIGS. 31 to 33 are parametric maps of the number of double bounds ndb, the number of methylene interrupted double bounds nmidb and the chain length CL in VAT performed in an obese subject. The maps are derived from native parametric maps after the application of a four-cluster mask to segment VAT;

FIGS. 34 to 36 are parametric maps of the number of double bounds ndb, the number of methylene interrupted double bounds nmidb and the chain length CL in liver performed in an obese subject. The maps are derived from native parametric maps after the application of a four-cluster mask to segment liver. The maps of FIGS. 28 to 36 clearly illustrate the differences in fatty acid composition between the fatty liver (more saturated) and the adipose tissues.

Figure 37:
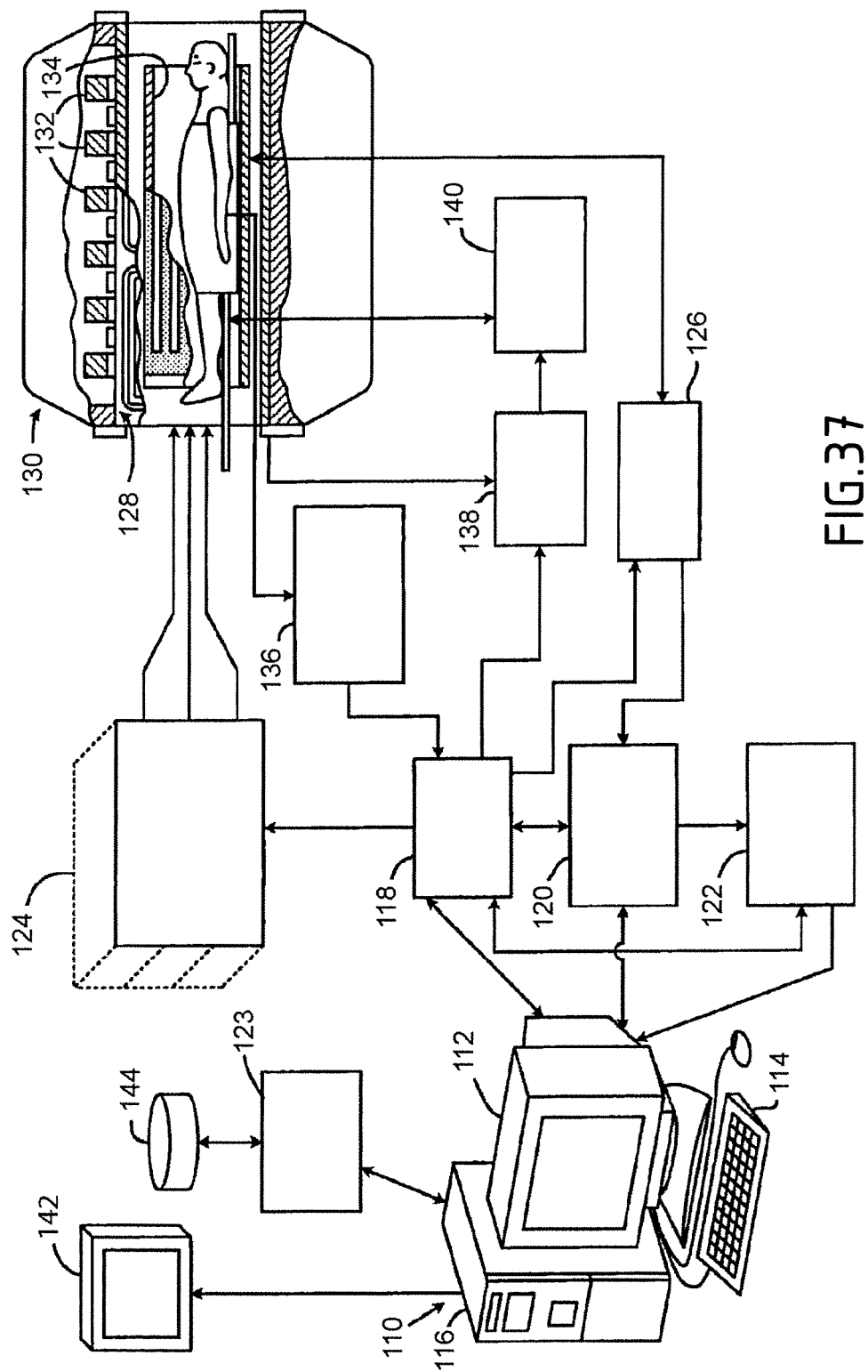

FIG. 37 is a schematic representation of a device for monitoring the proportion of unsaturated fatty acids and proportion of saturated fatty acids in a region of interest in a subject.

DETAILED DESCRIPTION OF SOME EMBODIMENTS

Figure 1:
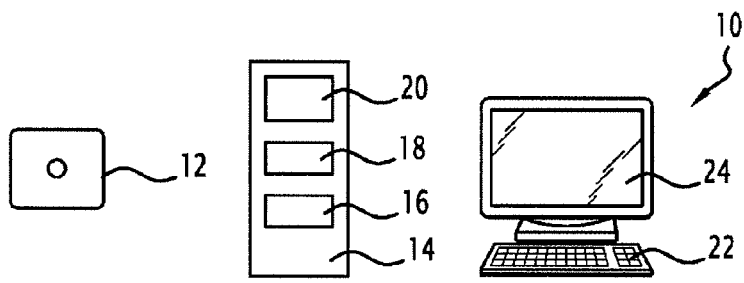
FIG. 1 shows schematically a system and a computer program product whose interaction enables to carry out a method for post-processing images.

A system 10 and a computer program product 12 are represented in FIG. 1. The interaction between the computer program product 12 and the system 10 enables to carry out a method for post-processing images.

System 10 is a computer. In the present case, system 10 is a laptop.

More generally, system 10 is a computer or computing system, or similar electronic computing device adapted to manipulate and/or transform data represented as physical, such as electronic, quantities within the computing system's registers and/or memories into other data similarly represented as physical quantities within the computing system's memories, registers or other such information storage, transmission or display devices.

System 10 comprises a processor 14, a keyboard 22 and a display unit 24.

The processor 14 comprises a data-processing unit 16, memories 18 and a reader 20. The reader 20 is adapted to read a computer readable medium.

The computer program product 12 comprises a computer readable medium.

The computer readable medium is a medium that can be read by the reader of the processor. The computer readable medium is a medium suitable for storing electronic instructions, and capable of being coupled to a computer system bus.

Such computer readable storage medium is, for instance, a disk, a floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

A computer program is stored in the computer readable storage medium. The computer program comprises one or more stored sequence of program instructions.

The computer program is loadable into the data-processing unit and adapted to cause execution of the method for post-processing images when the computer program is run by the data-processing unit.

Figure 2:
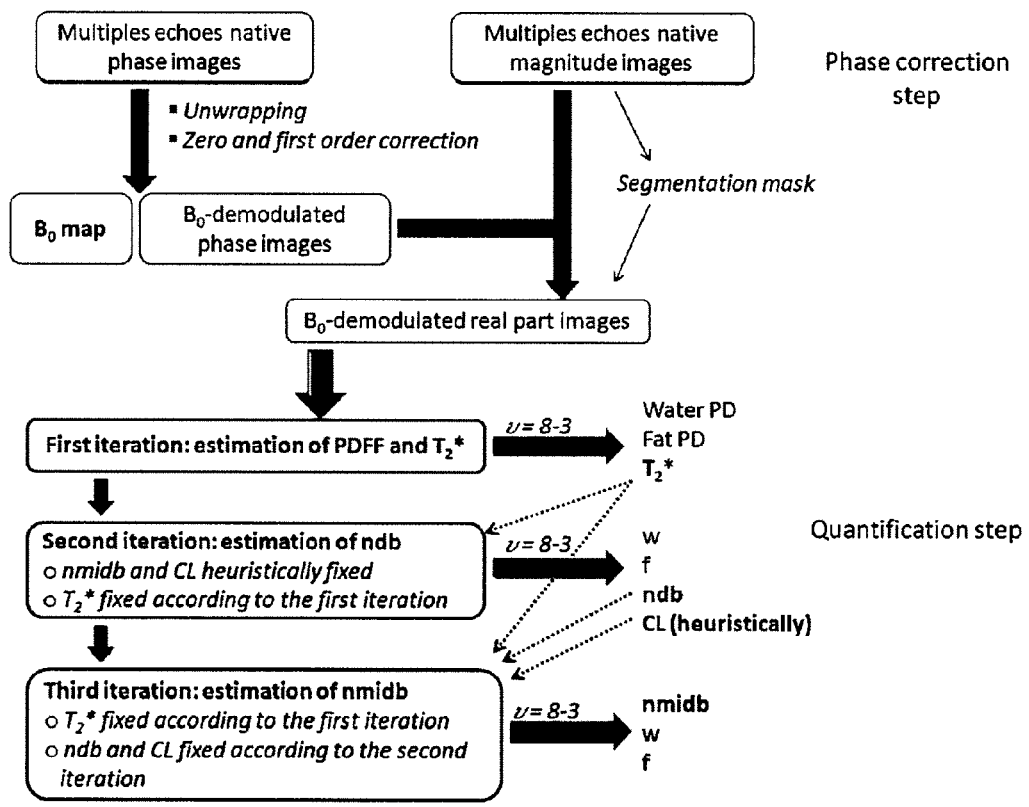
FIG. 2 shows a flowchart of the method for post-processing images.
Figure 3:
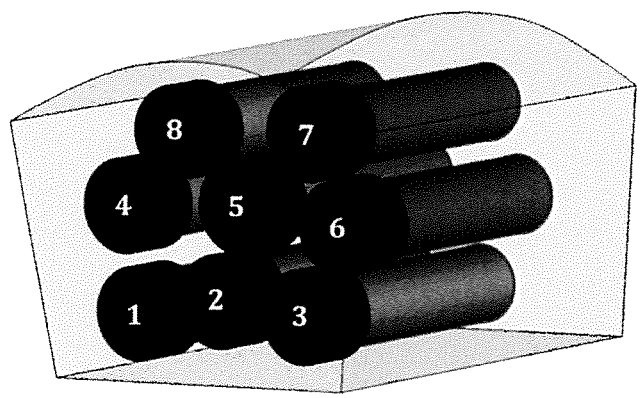
FIGS. 3 and 4 shows the scheme of the phantom built for in vitro experiments. Each vial is filled with different oils and is immersed in a sonographic gel for coil loading and minimizing the number of water/air interfaces. Number 1 corresponds to peanut, number 2 to canola, number 3 to sunflower, number 4 to sesame, number 5 to walnut, number 6 to olive, number 7 to grape seed and number 8 to hazelnut.
Figure 4:
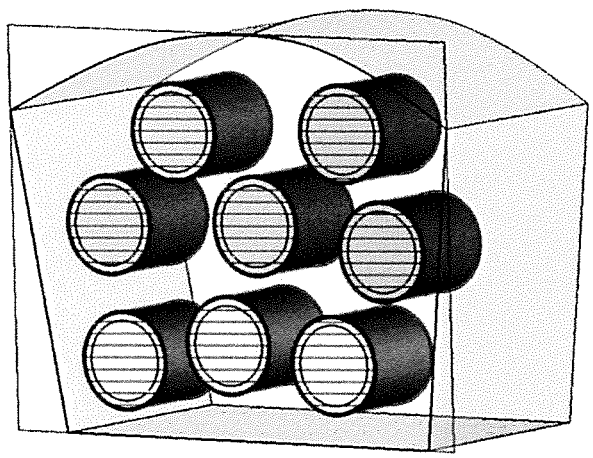

Operation of the system 10 is now described by illustrating an example of carrying out the method for post-processing images as illustrated by the flowchart of FIG. 2.

The images post-processed in the method for post-processing images are images of a region of interest in a subject.

The region of interest is adipose tissues or tissue containing fat

The subject is usually human beings.

In the experience described in reference with FIGS. 2 to 36, the subjects are human beings.

The images are acquired with a magnetic resonance imaging technique.

The magnetic resonance imaging technique involving successive echoes of a multiple-gradient echo sequence.

According to the specific embodiment described, the multiple-gradient echo sequence is a spoiled gradient echo sequence.

In addition, the magnetic resonance imaging technique is carried out by a clinical system operating at magnetic field with a magnitude of 3.0 Tesla (T).

Each image associates to each pixel of the image the amplitude of the measured signal in the magnetic resonance imaging technique and the phase of the measured signal in the magnetic resonance imaging technique.

In other words, for each image, it can be defined a magnitude map and a phase map.

The method for post-processing images comprises four steps, which are a step of correcting, a step of extracting, a step of calculating and a step of quantifying.

At the step of correcting, a two-cluster segmentation mask is built from the magnitude images to suppress background and air cavities with a k-means approach and was applied on the phase images.

Then, the multiple echo phase images are unwrapped by adding multiples of $\pm 2\pi$ when absolute jumps between consecutive elements of the array were greater than or equal to a jump tolerance of π radians.

From the unwrapped phase images, the zero-order phase (linked to radiofrequency penetration and eddy current effect) and the first-order phase (linked to local $B_0$ heterogeneities) are extracted pixel-by-pixel.

This procedure is achieved with a weighted linear least-square fit accounting for the phase to noise ratio difference occurring with $T_E$ and using the spoiled gradient echo sequence model for the MR signal phase $\varphi(T_E)$:

$$\varphi(T_E) = \varphi_0 + \varphi_1 T_E$$

wherein:
$\varphi_0$ accounts for the zero order phase (in rad) and
$\varphi_1$ for the first order phase (in rad·s$^{-1}$).
$B_0$ field heterogeneity ($\Delta B_0$) is deduced using $\Delta B_0 = \varphi_1/2\pi$.

This enables to correct multiple echoes phase images for zero and first order phase. Then, real part images are generated from the native magnitude images and the corrected phase images.

At the end of the correcting step, corrected real images are obtained.

Optionally, at the correcting step, phase images for zero (time independent) and first order (time-dependent) dephasings are also corrected.

Alternatively, the method for post-processing images comprises a step of providing corrected real images to be post-processed.

At the step of extracting, a real signal over echo time for at least one pixel of the unwrapped images is extracted.

According to the specific embodiment described, from multiple echo unwrapped real images, a real signal over echo time $S(T_E)$ is extracted pixel by pixel.

At the end of the extracting step, for each pixel, the real signal over echo time $S(T_E)$ is known.

At the step of calculating, fat characterization parameters are calculated by using a fitting technique applied on a model.

The model is a model for the real gradient echo signal at time $T_E$ from a pixel containing water and fat with an unknown number of spectral components.

In other words, such model is a function which associates to a plurality of parameters each extracted real signal.

This means that the model is fitted to the extracted real signal in order to derive a plurality of parameters. The plurality of parameters comprises at least two fat characterization parameters.

According to a specific embodiment, the fat characterization parameters are chosen in the group consisting of the number of double bounds ndb, the number of methylene-interrupted double bounds nmidb and the chain length CL.

The model is based on eight separate fat resonances.

The calculating step comprises several sub-steps of calculating by using the model in which at least one parameter is fixed.

Usually, the fixed parameter(s) differ from one sub-step to another.

In other words, a stepwise fitting approach is proposed to reduce and keep a constant degree of freedom v as can be seen on FIG. 2.

More precisely, the calculating step comprises three sub-steps of calculating in the illustrated example.

During the first sub-step of calculating, separation of fat and water proton densities ($PD_f$ and $PD_w$) is performed with a 3-parameter bi-exponential model of the real part of the signal ($S_{real}$) integrating the modeling of eight fat resonances.

Equation of $S_{real}$ over TE at steady state conditions with $T_1$ contribution neglected and $B_0$ heterogeneity corrected is:

$$S_{real}(TE) = \text{real}\left(\left(PD_w + PD_f \times \sum_{k=1}^{8} C_k\, e^{2\pi i f_k TE}\right) \times e^{-\frac{TE}{T_2^*}}\right)$$

Where:
$S_{real}(TE)$ is the real part of signal according to echo time;
$T_2^*$ is the transversal decay;
$C_k$ are coefficients equal to the ratio of the fat resonance k signal over the total fat signal, and
$f_k$ corresponds to the frequency shift between water and each fat resonance k.

$C_k$- and $f_k$-values used in this model were reported in Table 1 (see below).

From this first sub-step, the proton density fat fraction (PDFF) is calculated as $\text{PDFF} = [PD_f/(PD_f + PD_w)] \times 100$.

During the second sub-step, the fat spectrum model is modified as follows: the fat components are expressed according to their number of protons and to ndb, nmidb and CL.

The equation of $S_{real}$ over echo time at steady state conditions with $T_1$ contribution neglected and $B_0$ heterogeneity corrected can be expressed as follows:

$$S_{real}(TE) = \text{real}\left(\left(w \times n_{water} + f \times \sum_{k=1}^{8} n_k(ndb, CL, nmidb)\, e^{2\pi i f_k TE}\right) \times e^{-\frac{TE}{T_2^*}}\right)$$

Where
w and f represent the number of water and triglycerides molecules respectively,
$n_k$ (ndb, CL, nmidb) the number of protons in the fat spectrum component k according to ndb, CL and nmidb (see table 1 below),
$f_k$ the frequency shift between water and each fat spectrum component k,
$n_{water}$ the number of proton in a water molecule and
$T_2^*$ the transversal decay.

During the second sub-step, CL and nmidb are expressed according to ndb using the two heuristic approximations such as:

$$CL = 16.8 + 0.25 \times ndb,$$

and $$nmidb = 0.093 \times ndb^2.$$

In addition, $T_2^*$ value was used from the previous step. Thus, the fitted parameters are w, f and ndb.

During the third sub-step, the fitting procedure is reiterated to fit w, f and nmidb. The $T_2^*$-value is used from the first sub-step and the ndb-value from the second step. No fitting procedure is conducted to extract CL because this parameter does not give additional information about fatty acid composition saturation.

For each calculation sub-step, the fitting technique is performed with a non-linear least-square fitting technique using pseudo-random initial conditions.

As an example, the parameters may be derived by using a non-linear least-square fit using the multi-start Levenberg-Marquardt algorithm.

In mathematics and computing, the Levenberg-Marquardt algorithm (LMA), also known as the damped least-squares method, is used to solve non-linear least squares problems. These minimization problems arise especially in least squares curve fitting.

The LMA interpolates between the Gauss-Newton algorithm (GNA) and the method of gradient descent. The LMA is more robust than the GNA, which means that in many cases it finds a solution even if it starts very far off the final minimum. For well-behaved functions and reasonable starting parameters, the LMA tends to be a bit slower than the GNA. LMA can also be viewed as Gauss-Newton using a trust region approach.

The LMA is a very popular curve-fitting algorithm used in many software applications for solving generic curve-fitting problems. However, as for many fitting algorithms, the LMA finds only a local minimum, which is not necessarily the global minimum.

A multi-start technique or the use of pseudo-random initial conditions corresponds to the use of a grid of pseudo-random initial conditions. This enables to improve the robustness of optimization and avoid multiple local minima problem.

In other words, the fitting technique is carried out a certain number of times, each time corresponding to different initial conditions.

For instance, the number of times is superior or equal to five, preferably superior or equal to ten, more preferably superior or equal to twenty.

According to a specific example, the number of times is equal to fifty. This enables to improve the robustness and reliability of optimization, but also to avoid multiple local minima problem.

At the end of the calculating step, the fat characterization parameters are obtained.

At the step of quantifying, the proportion of unsaturated fatty acids and the proportion of saturated fatty acids in the region of interest in the subject are obtained based on the calculated fat characterization parameters.

Preferably, at the step of quantifying, the proportions of saturated, monounsaturated and polyunsaturated fatty acids in the region of interest in the subject are quantified based on the calculated fat characterization parameters.

As an example, the quantifying step comprises determining the fatty acid composition based on the calculated fat characterization parameters.

For determining the fatty acid composition, it is proposed to use the following relations:

$$F_{UFA} = \frac{ndb - nmidb}{3}$$

$$F_{PUFA} = \frac{nmidb}{3}$$

Where:
$F_{UFA}$ is the unsaturated fatty acid fraction in %, and
$F_{PUFA}$ is the polyunsaturated fatty acid fraction in %.

Optionally, determining the fatty acid composition may also comprise deducing the monounsaturated fatty acid fraction, which is generally labeled $F_{MUFA}$. For this, the following equation may be used:

$$F_{MUFA} = F_{UFA} - F_{PUFA}$$

Optionally, determining the fatty acid composition may also comprise calculating the saturated fatty acid fraction, which is generally labeled $F_{SFA}$. For this, the following equation may be used:

$$F_{SFA} = 100 - F_{UFA}$$

The proposed method for post-processing differs from the previous approaches by using a specific phase correction (unwrapping, zero and first order phase correction) before the quantification step. This has the advantage of eliminating two fitting parameters (the initial phase and $B_0$ field heterogeneities).

Such modification has two consequences: first, the degree of freedom is reduced second; the required number of echoes is decreased. The use of a limited number of echoes reduces the repetition time, thus directly the acquisition time.

Therefore, the scan duration becomes compatible with apnea and the exploratory volume covers a large volume. This issue is very important for imaging of the liver and visceral fat and to our knowledge we are the first to measure the fatty acid composition of triglycerides in the liver with a clinically relevant magnetic resonance imaging method.

With this last approach, the complex field map was derived by a regularization of the residual function which may lead to multiple local minima along to the off-resonance dimension caused by phase wraps. To address this issue, strategies based upon the $B_0$ field smoothness as a priori knowledge are currently used to find the correct local minima.

The proposed reconstruction is not sensitive to the apparent field map discontinuities linked to phase wraps and can to be run with real rather than complex values reducing the bias in estimations.

Thus, images taken the context of clinical magnetic resonance imaging systems may be post-processed to calculate fat characterization parameters with a good accuracy thanks to the proposed method for post-processing.

Such method for post-processing images may notably be used in a method for predicting that the subject is at risk of suffering from an obesity related disease.

An obesity related disease is a cancer, type 2 diabetes, a heart disease, a liver disease or non-alcoholic fatty liver diseases (NAFLD). Nonalcoholic fatty liver disease (NAFLD) and its most severe form, nonalcoholic steatohepatitis (NASH), are associated with high fat diet, high triglyceride levels, obesity, the metabolic syndrome and type II diabetes, and pose an increased risk of cardio vascular disease. NAFLD is an accumulation of fat in the liver that is not a result of excessive consumption of alcohol. 15% to 25% of cases of NAFLD progress and are associated with inflammation and liver damage; this condition is referred to as NASH. NASH is associated with an increased risk of developing liver cirrhosis and subsequence complications, including hepatocellular carcinoma.

The method for predicting comprises a step of carrying out the steps of the method for post-processing images of the subject as previously described, to obtain fat characterization parameters.

The method for predicting also comprises a step of predicting that the subject is at risk of suffering from the obesity related disease based on the fat characterization parameters.

Such method for post-processing images may also be used in a method for diagnosing an obesity related disease.

The method for diagnosing comprises a step of carrying out the steps of the method for post-processing images of the subject as previously described, to obtain fat characterization parameters.

The method for diagnosing also comprises a step of diagnosing the obesity related disease based on the fat characterization parameters.

Such method for post-processing images may also be used in a method for monitoring the responsiveness of a subject suffering from an obesity related disease to a treatment useful for said disease. The method for monitoring the responsiveness comprising a step of carrying out the steps of the method for post-processing images of the subject as previously described, to obtain fat characterization parameters before the treatment, a step of carrying out the steps of the method for post-processing images of the subject as previously described, to obtain fat characterization parameters during or after the treatment, and a step of comparing the fat characterization parameters before the treatment with the fat characterization parameters during or after the treatment, a difference between said fat characterization parameters being indicative that the treatment is effective.

Such method for post-processing images may also be used in a method for screening a probiotic, a prebiotic, a chemical compound or a biological compound suitable for obtaining a treatment useful for an obesity related disease using the method for monitoring the responsiveness of a subject as previously described.

Such method for post-processing images may also be used in a method for monitoring the proportion of unsaturated fatty acids and proportion of saturated fatty acids in the region of interest in the subject.

The method for monitoring comprises three steps: imaging, carrying out and quantifying.

At the step of imaging, the region of interest in the subject is imaged by using a magnetic resonance imaging technique, the magnetic resonance imaging technique involving successive echoes of a multiple-gradient echo sequence, to obtain images.

According to a specific embodiment, the magnetic resonance imaging technique involves using a magnetic field value comprised between 1.0 T and 11.7 T.

According to a more specific embodiment, the magnetic resonance imaging technique involves using a magnetic field value comprised between 1.5 T and 3.0 T.

At the step of carrying out, the steps of the method for post-processing images of the subject as previously described are carried out to obtain fat characterization parameters.

At the step of quantifying, the proportion of unsaturated fatty acids and the proportion of saturated fatty acids in the region of interest in the subject are quantified based on the calculated fat characterization parameters.

Preferably, at the step of quantifying, the proportion of saturated, monounsaturated and polyunsaturated fatty acids in the region of interest in the subject are quantified based on the calculated fat characterization parameters.

Such method for monitoring is a non-invasive which can be carried out in vivo, ex vivo and in vitro.

Such method may be implemented on a device for monitoring the proportion of unsaturated fatty acids and proportion of saturated fatty acids in the region of interest in the subject.

An example of such device is illustrated on FIG. 37.

The device comprises a controller 110, four servers and a magnetic resonance imaging system 138. The four servers are a pulse sequence server 118, a data acquisition server 120, a data processing server 122 and a data store server 123.

The controller 110 is adapted to receive the obtained images of the region of interest from the magnetic resonance imaging system 138, each image associating to each pixel of the image the amplitude of the measured signal in the magnetic resonance imaging technique and the phase of the measured signal in the magnetic resonance imaging technique.

The controller 110 is also adapted to unwrap the phase of each image, to obtain unwrapped images.

The controller 110 is further adapted to extract a real signal over echo time for at least one pixel of the unwrapped images, to obtain at least one real complex signal.

The controller 110 is also adapted to calculate fat characterization parameters by using the fitting technique previously described.

The controller 110 is also adapted to quantify the proportion of unsaturated fatty acids and proportion of saturated fatty acids in the region of interest in the subject based on the calculated fat characterization parameters.

Preferably, the controller 110 is also adapted to quantify the proportion of unsaturated, monounsaturated and polyunsaturated fatty acids in the region of interest in the subject based on the calculated fat characterization parameters.

The controller 110 provides the operator interface which enables scan prescriptions to be entered into the magnetic resonance imaging system 138.

According to the embodiment of FIG. 33, the controller 110 is a workstation.

The controller 110 comprises a display 112, a keyboard 114, a processor 116.

The processor 116 is a commercially available programmable machine running a commercially available operating system.

The controller 110 is coupled to the four servers 118, 120, 122 and 123.

According to the example of FIG. 33, the data store server 123 is performed by the processor 116 and associated disc drive interface circuitry.

The remaining three servers 118, 120 and 122 are performed by separate processors mounted in a single enclosure and interconnected using a 64-bit backplane bus. The pulse sequence server 118 employs a commercially available microprocessor and a commercially available quad communication controller. The data acquisition server 120 and data processing server 122 both employ the same commercially available microprocessor and the data processing server 122 further includes one or more array processors based on commercially available parallel vector processors.

The controller 110 and each processor for the servers 118, 120 and 122 are connected to a serial communications network. This serial network conveys data that is downloaded to the servers 118, 120 and 122 from the controller 110. The network conveys tag data that is communicated between the servers 118, 120, 122 and 123 and between the controller 110. In addition, a high speed data link is provided between the data processing server 122 and the workstation 10 in order to convey image data to the data store server 123.

The pulse sequence server 118 functions in response to program elements downloaded from the controller 110 to operate a gradient system 124 and an RF system 126. Gradient waveforms necessary to perform the prescribed scan are produced and applied to the gradient system 124 which excites gradient coils in an assembly 128 to produce the magnetic field gradients $G_x$, $G_y$ and $G_z$ used for position encoding nuclear magnetic resonance NMR signals. NMR is a physical property according to which the nuclei of atoms absorb and re-emit electromagnetic energy at a specific resonance frequency in the presence of a magnetic field.

The gradient coil assembly 128 forms part of a magnet assembly 130 which includes a polarizing magnet 132 and a whole-body RF coil 134.

RF excitation waveforms are applied to the RF coil 134 by the RF system 126 to perform the prescribed magnetic resonance pulse sequence. Responsive NMR signals detected by the RF coil 134 are received by the RF system 126, amplified, demodulated, filtered and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 134 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal.

The magnitude of the received NMR signal may thus be determined at any sampled point by the square root of the sum of the squares of the I and Q components:

$$M = \sqrt{I^2 + Q^2}$$

and the phase of the received NMR signal may also be determined by the following equation:

$$\Phi = \tan^{-1}\left(\frac{Q}{I}\right)$$

The pulse sequence server 118 also optionally receives patient data from a physiological acquisition controller 136. The controller 136 receives signals from a number of different sensors connected to the subject, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 138 which receives signals from various sensors associated with the condition of the subject and the magnet system. It is also through the scan room interface circuit 138 that a subject positioning system 140 receives commands to move the subject to desired positions during the scan.

It should be apparent that the pulse sequence server 118 performs real-time control of magnetic resonance imaging system elements during a scan. As a result, the hardware elements of the pulse sequence server 118 are operated with program instructions that are executed in a timely manner by run-time programs. The description components for a scan prescription are downloaded from the controller 110 in the form of objects. The pulse sequence server 118 contains programs which receive these objects and converts them to objects that are employed by the run-time programs.

The digitized NMR signal samples produced by the RF system 126 are received by the data acquisition server 120. The data acquisition server 120 operates in response to description components downloaded from the controller 110 to receive the real-time NMR data and provide buffer storage such that no data is lost by data overrun. In some scans the data acquisition server 120 does little more than pass the acquired NMR data to the data processor server 122. However, in scans which require information derived from acquired NMR data to control the further performance of the scan, the data acquisition server 120 is programmed to produce such information and convey it to the pulse sequence server 118. For example, during prescans NMR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process NMR signals used to detect the arrival of contrast agent in an MRA scan. In all these examples the data acquisition server 120 acquires NMR data and processes it in real-time to produce information which is used to control the scan.

The data processing server 122 receives NMR data from the data acquisition server 120 and processes it in accordance with description components downloaded from the controller 110. Such processing may include Fourier transformation of raw k-space NMR data to produce two or three-dimensional images.

Images reconstructed by the data processing server 122 are conveyed back to the controller 110 where they are stored. Real-time images are stored in a data base memory cache (not shown) from which they may be output to operator display 112 or a display 142 which is located near the magnet assembly 130 for use by attending physicians. Batch mode images or selected real time images are stored in a host database on disc storage 144. When such images have been reconstructed and transferred to storage, the data processing server 122 notifies the data store server 123 on the controller 10.

The magnetic resonance imaging system 138 is adapted to image the region of interest in the subject by using a magnetic resonance imaging technique, the magnetic resonance imaging technique involving successive echoes of a multiple-gradient echo sequence, to obtain images.

The magnetic resonance imaging system 138 is further adapted to apply a magnetic field whose magnetic field value comprised between 1.0 T and 11.7 T.

According to a specific embodiment, the magnetic resonance imaging system 138 is adapted to apply a magnetic field whose magnetic field value comprised between 1.5 T and 3.0 T.

Experimental Section

MR Acquisition

Acquisitions were performed on a Philips Ingenia 3.0 T system (Philips, Best, The Netherlands) with 40 mT·m$^{-1}$ gradient amplitude. A 3D spoiled-gradient multiple echo sequence (3D T$_1$ FFE) with parallel imaging and sensitivity encoding (SENSE) was used, as well as a 32-channel phase array body coil and multi transmit parallel radiofrequency transmission technology. Acquisition parameters were:
  TR/flip angle equal to 10 ms/3°;
  SENSE factors, 1.5 and 1.8 according to slice and phase direction respectively;
  2000 Hz·pixel-1 receiver bandwidth and
  2 signal averages.
Geometric parameters were:
  field of view, 420×380×160 mm3;
  acquisition matrix, 140×128×20 (256$^2$ after interpolation).

Twenty slices of 8 mm thickness (40 of 4 mm after interpolation) in the transverse plane were acquired using eight echoes: n×1.15 ms with n=1, . . . , 8. Total scan duration was 20 s. Phase and magnitude images were saved systematically. This protocol was used for both phantom and in vivo imaging.

Post-Processing Algorithm

The post-processing algorithm was developed with Matlab r2012a (The MathWorks, Natick, Mass.).

The post-processing algorithm corresponds to the method for post-processing images as previously described.

Computer Simulation

Computer simulations were performed to evaluate the error which may occur on each quantified parameter (T2*, $\Delta B_0$, ndb and nmidb) with our stepwise approach according to the FA composition.

A complex signal including eight fat components and water was first generated. Each component was expressed according to ndb, nmidb and CL (Table 1).

TABLE 1

Parameters conditioning the fat spectrum models used in our study. These parameters are $C_k$: ratio of fat resonance k signal over total fat signal, $f_k$: frequency shift between water and each fat resonance k, $n_k$ (ndb, CL, nmidb): number of protons of fat spectrum component k according to ndb, CL and nmidb, ndb: number of double bounds, nmib: number of methylene interrupted double bonds and CL: chain length.

| Component k | Type | $C_k$ | $n_k$(ndb, CL, nmidb) | $f_k$ (Hz) |
|---|---|---|---|---|
| 1 | olefinic | 0.037 | 2 × ndb + 1 | −75.3 |
| 2 | glycerol | 0.039 | 4 | 63.9 |
| 3 | dyacil | 0.006 | 2 × nmidb | 249 |
| 4 | α-Carboxyl | 0.058 | 6 | 314 |
| 5 | α-olefinic | 0.062 | 4 × (ndb − nmidb) | 342 |
| 6 | β-carboxyl | 0.058 | 6 | 396 |
| 7 | methylene | 0.642 | (6 × (CL − 4)) − (ndb × 8) + (nmidb × 2) | 434 |
| 8 | methyl | 0.088 | 9 | 485 |

R2* relaxivity of each component was provided using the relationship $R2^* = R2 + R2'$ Fat R2-values were taken from literature.

Water R2 was chosen as being close to liver R2 (i.e. water R2=1/34 ms).

Zero order phase was fixed at 0.5 rad and first order phase (i.e. $\Delta B_0$) at 50 Hz.

R2' was chosen to reproduce a water T2* equal to 20 ms (i.e. R2'=0.02 ms$^{-1}$).

Each resonance was considered equally affected by $B_0$ field heterogeneities and susceptibility effects.

T2* was as follows:
water, 20 ms;
olefinic group, 23.8 ms;
glycerol 18.8 ms;
diacyl 24.2 ms;
α-carboxyl, 23.4 ms;
α-olefinic, 20.8 ms;
β-carboxyl, 21.2 ms;
methylene, 30.6 ms and
methyl, 30.1 ms.

Number of triglyceride (f) and water molecules (w) was chosen to obtain a PDFF equal to 30%. Complex Gaussian noise was added to obtain a SNR equal to 100. From this signal phase and magnitude were taken ndb-values varied from 0.05 to 6 with 0.05 increments and nmidb from 0.025 to 3 with 0.025 increments.

$120^2$ signals were computed and the method for post-processing was applied on each simulation. Error ($\xi_{F_v}$) maps according to (ndb, nmidb) pairs were computed for each target value (Tv) according to:

$$\xi_{F_v}(ndb, nmidb) = \left(\frac{|T_v - F_v|}{T_v}\right) \times 100$$

Where $F_v$ is the fitted value.

Phantom Experiment

A phantom was made by filling eight vials with different oils: olive, sesame, sunflower, walnuts, peanuts, hazelnuts, grape seed and canola. The vials were immersed in a sonographic gel (EDM imaging, Sarcelles, France) for coil loading and minimizing the number of water/air interfaces that may produce susceptibility artifacts. The phantom scheme is given in FIGS. 3 and 4. The vials were scanned with the MR protocol described above.

The chemical composition of each oil (i.e. the proportion of each fatty acid) was obtained.

Theoretical ndb was calculated thanks to the following formula:

$$ndb = \left(\frac{1}{M}\sum_n^1 n \times m_{UFAn}\right) \times 3$$

where:
$m_{UFAn}$ is the mass of an UFA group with n double bonds, and
M is the total mass.

Theoretical CL was calculated according to the mathematical formula that follows:

$$CL = \frac{1}{M}\Sigma n_C \times m_{FAnc}$$

where:
$m_{FAnc}$ is the mass of a FA group with a chain composed of $n_C$ carbons, and
M is the total mass.

Theoretical nmidb was calculated according to:

$$nmidb = \left(\frac{m_{PUFA}}{M}\right) \times 3$$

where:
$m_{PUFA}$ is the mass of a PUFA group, and
M is the total mass.

To evaluate the reproducibility of this method, test-retests were performed in the phantom at two different time points. The results are expressed as mean±standard deviation for each oil and coefficient of variation (CV) was computed as the ratio of the standard deviation to the mean. Comparison between theoretical and experimental data was performed using linear regression.

In Vivo Study

Two healthy obese volunteers (1 man, 1 woman; mean age: 29±3 years; mean body mass index: 35±2 kg·m$^{-2}$) and 3 patients with suspected liver steatosis (2 men, 1 woman; mean age: 56±20 years; mean body mass index<30 kg·m$^{-2}$) had a magnetic resonance imaging examination with the same protocol used for the phantom experiments and described above. The image acquisitions were performed with breath-holding. The protocol was approved by the local ethics committee and informed consent was obtained.

Fat and water only, PDFF, T2*, $\Delta B_0$, ndb, nmidb and CL maps were generated in the phantoms and the human subjects. From the subjects PDFF maps, masks were built using a dedicated segmentation algorithm combining an active contour approach with mathematical morphology to segment the liver, the subcutaneous adipose tissue (SAT) and the visceral adipose tissue (VAT). Then, the mask was applied on each parametric map to measure the mean value of the key parameters (PDFF, ndb, nmidb, CL and T2*) in each compartment.

Results of the Computer Simulations

Mean errors ($\xi_{T2^*}$) on all (ndb,nmidb)-pairs investigated here were:
- (2.8±1.6)% for the value of $T_2^*$ of water,
- (34.2±2.1)% for the value of $T_2^*$ of methyl,
- (35.1±2.1)% for the value of $T_2^*$ of methylene,
- (6.5±2.9)% for the value of $T_2^*$ of β-carboxyl,
- (4.7±2.8)% for the value of $T_2^*$ of α-olefinic,
- (17.2±2.6)% for the value of $T_2^*$ of α-carboxyl,
- (18.2±2.6)% for the value of $T_2^*$ of diacyl,
- (5.6±3.3)% for the value of $T_2^*$ of glycerol, and
- (16.5±2.7)% for the value of $T_2^*$ of olefinic.

Concerning $B_0$, $\xi_{B0}$ was equal to 2.4±1.7%.

Figure 5:
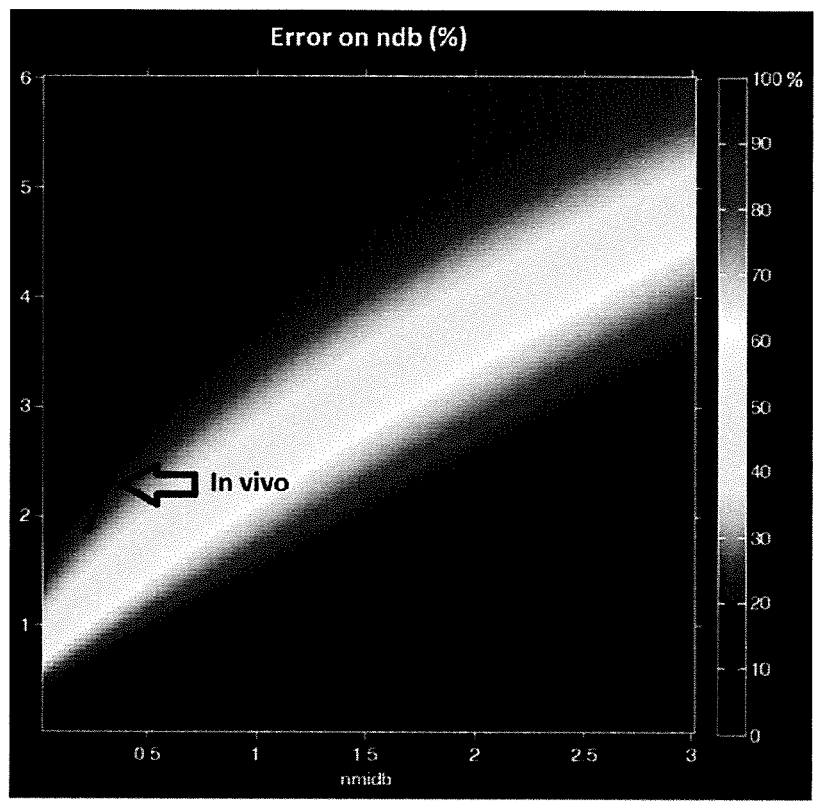
FIGS. 5 and 6 illustrates in a graph the quantification errors on the number of double bounds ndb and the number of methylene interrupted double bounds nmidb according to the fatty acid composition. The black line represents the quadratic pattern of fatty acid composition of in vivo and vegetable oils triglycerides according to ndb and nmidb. The error notably varies according to fatty acid composition.
Figure 6:
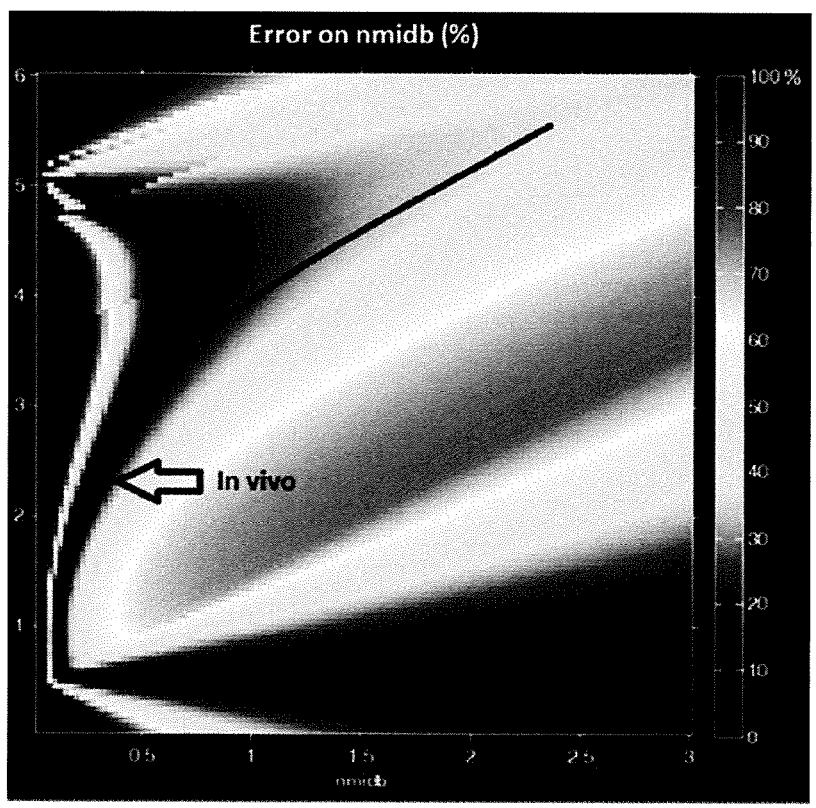
Figure 9:
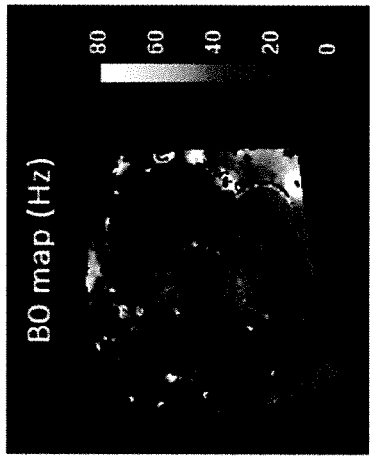
Figure 12:
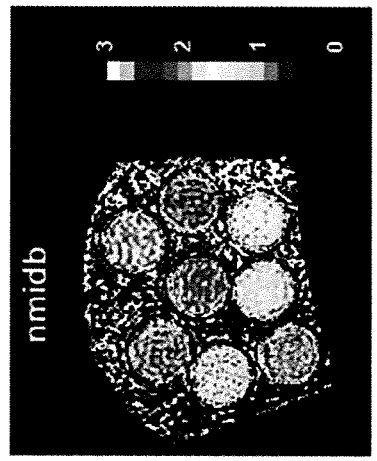
Figure 8:
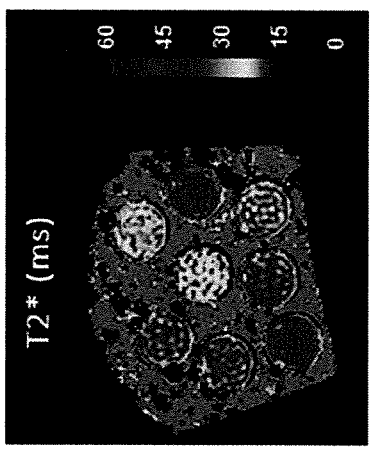
Figure 11:
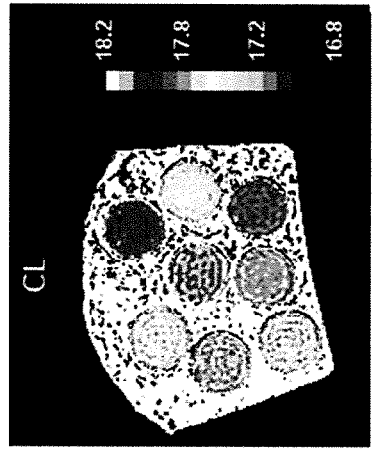
Figure 7:
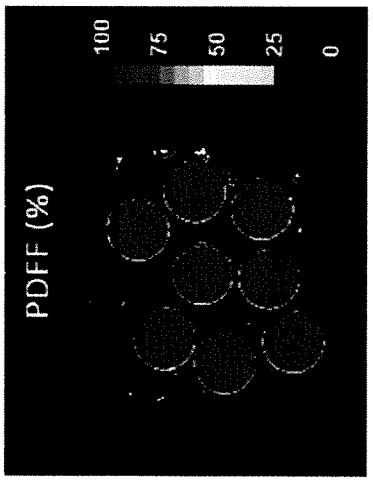
Figure 10:
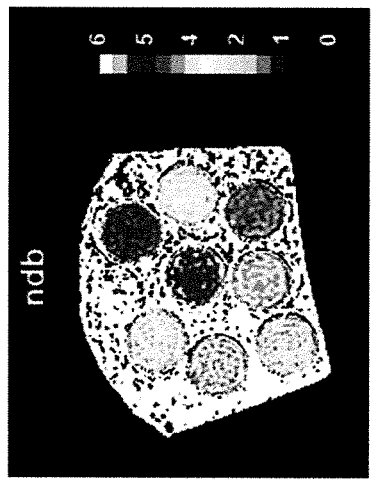

By contemplating FIGS. 5 and 6, it appears that regarding the values of ndb and nmidb, ξ varied notably according to FA composition. Nevertheless, for FA composition range of in vivo and vegetable oil triglycerides (see black lines in FIGS. 5 and 6), $\xi_{ndb}$ and $\xi_{nmidb}$ were not greater than 10%.

Results of the Phantom Experiment

As expected in the phantom, mean PDFF measured from all vials was close to 100% and ranged from 95.5±0.2% (walnut oil) to 99.8±0.7% (sesame oil). $T_2^*$ varied according to the oils and ranged from 21.8±0.1 ms (walnut oil) to 45.5±0.2 ms (olive oil). PDFF and $T_2^*$ measured oil-by-oil are reported in Table 2 which is reproduced below.

TABLE 2

Mean and standard deviation of PDFF and $T_2^*$ measured in the oils

|  |  | PDFF (%) | $T_2^*$ (ms) |
|---|---|---|---|
| Peanut | Test | 99.7 ± 0.6 | 43.5 ± 5.7 |
|  | Re-test | 99.6 ± 0.6 | 43.0 ± 5.6 |
| Canola | Test | 98.9 ± 1.0 | 39.9 ± 6.1 |
|  | Re-test | 98.6 ± 1.1 | 39.9 ± 6.0 |
| Sunflower | Test | 97.5 ± 1.5 | 33.7 ± 5.0 |
|  | Re-test | 97.9 ± 1.2 | 33.4 ± 5.0 |
| Olive | Test | 98.8 ± 1.0 | 45.3 ± 6.3 |
|  | Re-test | 99.0 ± 0.8 | 45.6 ± 6.2 |
| Walnut | Test | 95.3 ± 2.4 | 21.9 ± 2.9 |
|  | Re-test | 95.6 ± 2.6 | 21.8 ± 2.9 |
| Sesame | Test | 99.8 ± 0.5 | 36.1 ± 4.1 |
|  | Re-test | 99.7 ± 0.5 | 35.6 ± 4.0 |
| Hazelnut | Test | 99.6 ± 0.7 | 36.1 ± 4.8 |
|  | Re-test | 99.6 ± 0.6 | 36.6 ± 4.8 |
| Grape seed | Test | 97.3 ± 2.1 | 29.3 ± 4.7 |
|  | Re-test | 97.5 ± 2.0 | 29.1 ± 4.1 |

The number of double bonds ndb ranged from 2.83±0.10 (olive oil) to 5.24±0.19 (walnut oil). The number of methylene interrupted double bonds nmidb ranged from 0.60±0.31 (hazelnut oil) to 2.34±0.16 (walnut oil). The chain length CL ranged from 17.50±0.03 (olive oil) to 18.08±0.03 (walnut oil). In each vial, the parametric map was homogeneous as can be seen on FIGS. 7 to 12.

Coefficients of variations measured from the test-retests were smaller for ndb (median: 2.9%; range: 0.2-6.2%) than for nmidb (median: 16.6%; range: 0.4-51.9%). The theoretical ndb, CL and nmidb calculated from mass composition of each oil, and the measurements achieved oil-by-oil from test-retests are summarized in Table 3. Table 3 is reproduced below:

TABLE 3

Theoretical and measured ndb, nmidb and CL of the different oils (Th, Meas. and CV stand respectively for theoretical, measured and coefficient of variation)

|  |  | ndb | | nmidb | | CL | |
|---|---|---|---|---|---|---|---|
| Oil |  | Th | Meas. | Th | Meas. | Th | Meas. |
| Peanut | Test | 3.39 | 3.18 ± 0.29 | 1.01 | 1.15 ± 0.30 | 17.97 | 17.6 ± 0.12 |
|  | Re-test |  | 2.92 ± 0.19 |  | 0.87 ± 0.17 |  | 17.53 ± 0.06 |
|  | CV (%) |  | 6.0 |  | 19.6 |  | 0.2 |
| Canola | Test | 3.98 | 3.72 ± 0.19 | 1.05 | 1.17 ± 0.16 | 17.95 | 17.74 ± 0.04 |
|  | Re-test |  | 3.68 ± 0.19 |  | 0.94 ± 0.18 |  | 17.72 ± 0.05 |
|  | CV (%) |  | 0.8 |  | 15.4 |  | 0.08 |
| Sunflower | Test | 4.59 | 4.25 ± 0.19 | 1.95 | 1.68 ± 0.20 | 17.90 | 17.86 ± 0.05 |
|  | Re-test |  | 4.31 ± 0.19 |  | 1.67 ± 0.24 |  | 17.87 ± 0.06 |
|  | CV (%) |  | 1.0 |  | 0.4 |  | 0.04 |
| Olive | Test | 2.86 | 2.90 ± 0.27 | 0.32 | 0.72 ± 0.20 | 17.74 | 17.52 ± 0.05 |
|  | Re-test |  | 2.76 ± 0.21 |  | 0.55 ± 0.18 |  | 17.48 ± 0.06 |
|  | CV (%) |  | 3.5 |  | 18.9 |  | 0.2 |
| Walnut | Test | 5.40 | 5.10 ± 0.19 | 2.32 | 2.22 ± 0.23 | 17.84 | 18.06 ± 0.05 |
|  | Re-test |  | 5.37 ± 0.18 |  | 2.45 ± 0.15 |  | 18.10 ± 0.05 |
|  | CV (%) |  | 3.7 |  | 7.0 |  | 0.2 |
| Sesame | Test | 3.89 | 3.71 ± 0.36 | 1.32 | 1.50 ± 0.34 | 17.80 | 17.72 ± 0.09 |
|  | Re-test |  | 3.59 ± 0.28 |  | 1.18 ± 0.32 |  | 17.66 ± 0.07 |
|  | CV (%) |  | 2.3 |  | 16.9 |  | 0.3 |
| Hazelnut | Test | 3.05 | 3.12 ± 0.38 | 0.27 | 0.82 ± 0.35 | 17.91 | 17.58 ± 0.09 |
|  | Re-test |  | 2.86 ± 0.26 |  | 0.38 ± 0.19 |  | 17.49 ± 0.09 |
|  | CV (%) |  | 6.2 |  | 51.9 |  | 0.4 |
| Grape seed | Test | 4.98 | 4.68 ± 0.30 | 2.18 | 1.92 ± 0.22 | 17.90 | 17.94 ± 0.04 |
|  | Re-test |  | 4.67 ± 0.30 |  | 1.99 ± 0.31 |  | 17.96 ± 0.08 |
|  | CV (%) |  | 0.2 |  | 2.5 |  | 0.1 |

The linear regressions between measured and theoretical values were, as can be seen on FIGS. 13 and 14:

y=0.94x+0.25; $r^2$=0.99; p<0.0001 for ndb and y=0.77x+0.32; $r^2$=0.97; p<0.0001 for nmidb.

Linear regression showed a slight systematic underestimation of ndb in comparison with the theory. Regarding nmidb no systematic deviation was observed.

The UFA, PUFA, MUFA and SFA fractions calculated in each vial are summarized in Table 4. Such table 4 is reproduced below:

TABLE 4

Theoretical and measured UFA, SFA, PUFA and MUFA fractions of oils

| Oil | UFA (%) Th | UFA (%) Meas. | SFA (%) Th | SFA (%) Meas. | PUFA (%) Th | PUFA (%) Meas. | MUFA (%) Th | MUFA (%) Meas. |
|---|---|---|---|---|---|---|---|---|
| Peanut | 81 | 68 | 19 | 32 | 31 | 29 | 50 | 39 |
| Canola | 92 | 88 | 8 | 12 | 31 | 28 | 61 | 60 |
| Sunflower | 87 | 87 | 13 | 13 | 65 | 55 | 22 | 32 |
| Olive | 85 | 73 | 15 | 27 | 10 | 19 | 74 | 55 |
| Walnut | 85 | 97 | 15 | 3 | 84 | 81 | 1 | 16 |
| Sesame | 85 | 77 | 15 | 23 | 43 | 44 | 42 | 41 |
| Hazelnut | 93 | 80 | 9 | 20 | 10 | 10 | 83 | 70 |
| Grape seed | 93 | 91 | 7 | 9 | 73 | 68 | 20 | 23 |

Results of the In Vivo Study

In FIGS. 15 to 22, magnitude and phase native images obtained in an obese volunteer are provided. Wrap, zero and first order phase corrected images as well as real part images processed with the presented algorithm are also shown.

As further shown by FIGS. 23 to 36, $T_2^*$ relaxation times of the five subjects were:
(20.6±5.0) ms in liver,
(35.8±3.6) ms in SAT, and
(26.7±4.1) ms in VAT.

In addition, the PDFF was (21.7±6.80)% in liver, (93.0±1.0)% in SAT, and
(87.4±3.1)% in VAT.

Furthermore, the ndb/nmidb/CL parameters were:
1.80±0.25/0.51±0.21/17.43±0.07 in liver,
2.72±0.31/0.94±0.16/17.47±0.08 in SAT, and
2.53±0.21/0.84±0.14/17.43±0.07 in VAT.

Such results are also apparent in table 5 which is reproduced below:

UFA fractions were 43±9.5, 59±6.9 and 57±2.9% in the liver, SAT and VAT respectively.

$F_{PUFA}$ was 17±6.8, 31±5.4 and 28±4.8% in the liver, SAT and VAT respectively.

$F_{MUFA}$ was 26±14.2, 28±6.6 and 29±4.1% in the liver, SAT and VAT respectively.

$F_{SFA}$ were 57±9.5, 41±6.9 and 43±2.9% in the liver, SAT and VAT respectively.

CONCLUSION

A sequential MRI method for the quantification of the triglyceride FA composition is proposed. As demonstrated by the in vitro experiments, there was a strong agreement between ndb, nmidb and CL quantified with the presented method, and the theoretical values calculated using oil composition. In vivo, our results were consistent with previously published data.

In visceral adipose tissue, ndb measured in our study was in agreement with previous analysis. In the fatty liver, our results agreed with others experiments.

The coefficients of variation in the test-retest experiments suggest that our method is reproducible even if ndb appears more reproducible than nmidb. We attribute the slight differences observed between test and retest to changes linked to lipid peroxidation. Indeed, test and retest were performed with a time interval of several weeks and our vials were not protected against light exposure. Other confounding factors could be related to the experimental conditions such as temperature, which influences the water resonance shift.

To conclude, it has been shown the feasibility of a magnetic resonance imaging quantification method of the triglyceride FA composition at 3.0T. The in vivo results show that human applications are feasible in fatty liver and

TABLE 5

Key parameters (PDFF, $T_2^*$, ndb, nmidb and CL) measured in vivo, in fatty liver, SAT and VAT (BMI is expressed in kg · m$^{-2}$, PDFF in % and $T_2^*$ in ms).

| Subj | Age | Sex | BMI | Tissue | PDFF | $T_2^*$ | ndb | nmidb | CL |
|---|---|---|---|---|---|---|---|---|---|
| 1 | 27 | M | 34.1 | Liver | 27.9 ± 6.8 | 28.3 ± 5.6 | 1.82 ± 0.71 | 0.79 ± 0.32 | 17.26 ± 0.22 |
|   |    |   |      | SAT   | 92.5 ± 5.0 | 35.8 ± 14.1 | 2.93 ± 0.47 | 0.98 ± 0.26 | 17.52 ± 0.20 |
|   |    |   |      | VAT   | 83.0 ± 14.2 | 23.9 ± 15.7 | 2.50 ± 0.72 | 0.77 ± 0.35 | 17.42 ± 0.23 |
| 2 | 32 | F | 36.7 | Liver | 29.2 ± 3.0 | 15.3 ± 1.8 | 1.45 ± 0.51 | 0.51 ± 0.21 | 17.19 ± 0.18 |
|   |    |   |      | SAT   | 93.5 ± 2.8 | 35.3 ± 9.1 | 2.42 ± 0.32 | 0.87 ± 0.19 | 17.40 ± 0.08 |
|   |    |   |      | VAT   | 85.5 ± 9.8 | 25.2 ± 11.1 | 2.41 ± 0.50 | 0.80 ± 0.37 | 17.40 ± 0.19 |
| 3 | 41 | F | <30  | Liver | 20.2 ± 4.7 | 19.7 ± 2.2 | 1.97 ± 0.50 | 0.51 ± 0.17 | 17.31 ± 0.19 |
|   |    |   |      | SAT   | 92.8 ± 3.3 | 36.0 ± 10.1 | 2.39 ± 0.19 | 0.83 ± 0.18 | 17.38 ± 0.05 |
|   |    |   |      | VAT   | 89.1 ± 6.3 | 30.8 ± 11.1 | 2.28 ± 0.18 | 0.65 ± 0.19 | 17.34 ± 0.10 |
| 4 | 71 | M | <30  | Liver | 18.0 ± 3.9 | 17.3 ± 2.1 | 2.09 ± 0.18 | 0.52 ± 0.21 | 17.32 ± 0.19 |
|   |    |   |      | SAT   | 91.7 ± 2.7 | 31.0 ± 9.4 | 2.75 ± 0.36 | 0.81 ± 0.24 | 17.49 ± 0.18 |
|   |    |   |      | VAT   | 90.6 ± 6.8 | 22.3 ± 9.1 | 2.70 ± 0.49 | 1.01 ± 0.32 | 17.48 ± 0.18 |
| 5 | 49 | F | <30  | Liver | 13.1 ± 6.8 | 22.3 ± 5.1 | 1.76 ± 0.60 | 0.31 ± 0.20 | 17.27 ± 0.21 |
|   |    |   |      | SAT   | 94.4 ± 2.6 | 41.1 ± 7.0 | 3.1 ± 0.32 | 1.19 ± 0.21 | 17.57 ± 0.06 |
|   |    |   |      | VAT   | 88.7 ± 7.2 | 31.4 ± 10.2 | 2.78 ± 0.35 | 0.95 ± 0.25 | 17.50 ± 0.15 | adipose tissues. Ultimately, the quantification of the triglyceride FA composition with 3.0T magnetic resonance imaging has the potential to become a non-invasive clinical biomarker of fat-related disorders such as NASH.

LIST OF ABBREVIATIONS

In the description, the following abbreviations are used:
NAFLD: Non Alcoholic Fatty Liver Disease
NASH: Non Alcoholic Steato-Hepatitis
FA: Fatty Acid
SFA: Saturated Fatty Acid
MUFA: MonoUnsaturated Fatty Acid
PUFA: PolyUnsaturated Fatty Acid
NDB: Number of Double Bonds
NMIDB: Number of Methylene-Interrupted Double Bonds
CL: Chain Length
PDFF: Proton Density Fat Fraction
SAT: Subcutaneous Adipose Tissue
VAT: Visceral Adipose Tissue
SNR: Signal to Noise Ratio

The invention claimed is:

1. A method for post-processing images of a region of interest in a subject, the images being acquired with a magnetic resonance imaging technique, the magnetic resonance imaging technique involving successive echoes of a multiple-gradient echo sequence, each image associating to each pixel of the image the amplitude of the measured signal in the magnetic resonance imaging technique and the phase of the measured signal in the magnetic resonance imaging technique, the method for post-processing comprising at least the step of:
   unwrapping the phase of each image, to obtain unwrapped images,
   extracting a real signal over echo time for at least one pixel of the unwrapped images, to obtain at least one extracted real signal,
   calculating fat characterization parameters by using a fitting technique applied on a model,
   the model being a function which associates to a plurality of parameters each extracted real signal, the plurality of parameters comprising at least two fat characterization parameters and at least one parameter obtained by a measurement,
   the fitting technique being a non-linear least-square fitting technique using pseudo-random initial conditions.

2. The method for post-processing images according to claim 1, wherein the fat characterization parameters are chosen in the group consisting of the number of double bounds, the number of methylene-interrupted double bounds and the chain length.

3. The method for post-processing images according to claim 1, wherein the method for post-processing images further comprises the step of:
   measuring the field inhomogeneity in the magnetic field used in the magnetic resonance imaging technique, and
   measuring the transversal relaxivity rate or transversal relaxation time,
   the parameters obtained by a measurement the field inhomogeneity in the magnetic field used in the magnetic resonance imaging technique and the transversal relaxivity rate.

4. The method for post-processing images according to claim 1, wherein the calculating step comprises several sub-steps of calculating by using the model in which at least one parameter is fixed.

5. The method for post-processing images according to claim 1, wherein the method for post-processing images further comprises the step of:
   quantifying the proportion of unsaturated fatty acids and proportion of saturated fatty acids in the region of interest in the subject based on the calculated fat characterization parameters.

6. The method for post-processing images according to claim 5, wherein the quantifying step comprises determining the fatty acid composition based on the calculated fat characterization parameters.

7. A method for predicting that a subject is at risk of suffering from an obesity related disease, the method for predicting at least comprising the step of:
   carrying out the steps of the method for post-processing images of the subject according to claim 1, to obtain fat characterization parameters, and
   predicting that the subject is at risk of suffering from the obesity related disease based on the fat characterization parameters.

8. A method for diagnosing an obesity related disease, the method for diagnosing at least comprising the step of:
   carrying out the steps of the method for post-processing images of the subject according to claim 1, to obtain fat characterization parameters, and
   diagnosing the obesity related disease based on the fat characterization parameters.

9. A method for monitoring the responsiveness of a subject suffering from an obesity related disease to a treatment useful for said disease, the method for monitoring the responsiveness comprising:
   carrying out the steps of the method for post-processing images of the subject according to claim 1, to obtain fat characterization parameters before the treatment,
   carrying out the steps of the method for post-processing images of the subject according to claim 1, to obtain fat characterization parameters during or after the treatment, and
   comparing the fat characterization parameters before the treatment with the fat characterization parameters during or after the treatment, a difference between said fat characterization parameters being indicative that the treatment is effective.

10. A method for screening a probiotic, a prebiotic, a chemical compound or a biological compound suitable for obtaining a treatment useful for an obesity related disease using the method for monitoring the responsiveness of a subject according to claim 9.

11. A method for monitoring the proportion of unsaturated fatty acids and proportion of saturated fatty acids in a region of interest in a subject, the method for monitoring at least comprising the step of:
   imaging the region of interest in the subject by using a magnetic resonance imaging technique, the magnetic resonance imaging technique involving successive echoes of a multiple-gradient echo sequence, to obtain images
   carrying out the steps of the method for post-processing the obtained images according to claim 1, to obtain fat characterization parameters, and
   quantifying the proportion of unsaturated fatty acids and proportion of saturated fatty acids in the region of interest in the subject based on the calculated fat characterization parameters.

12. The method for monitoring according to claim 11, wherein the magnetic resonance imaging technique involves using a magnetic field value comprised between 1.0 T and 11.7 T.

13. A computer program product comprising instructions for carrying out the steps of a method according to claim 1 when said computer program product is executed on a suitable computer device.

14. A computer readable medium having encoded thereon a computer program according to claim 13.

15. A device for monitoring the proportion of unsaturated fatty acids and proportion of saturated fatty acids in a region of interest in a subject, the device comprising:
    a magnetic resonance imaging system adapted to image the region of interest in the subject by using a magnetic resonance imaging technique, the magnetic resonance imaging technique involving successive echoes of a multiple-gradient echo sequence, to obtain images and
    a controller adapted to:
        receive the obtained images of the region of interest from the magnetic resonance imaging system, each image associating to each pixel of the image the amplitude of the measured signal in the magnetic resonance imaging technique and the phase of the measured signal in the magnetic resonance imaging technique,
        unwrap the phase of each image, to obtain unwrapped images,
        extract a real signal over echo time for at least one pixel of the unwrapped images, to obtain at least one extracted real signal,
        calculate fat characterization parameters by using a fitting technique applied on a model,
        the model being a function which associates to a plurality of parameters each extracted real signal, the plurality of parameters comprising at least two fat characterization parameters and at least one parameter obtained by a measurement,
        the fitting technique being a non-linear least-square fitting technique using pseudo-random initial conditions, and
        quantify the proportion of unsaturated fatty acids and proportion of saturated fatty acids in the region of interest in the subject based on the calculated fat characterization parameters.

16. A device for monitoring according to claim 15, the magnetic resonance imaging system is adapted to apply a magnetic field whose magnetic field value comprised between 1.0 T and 11.7 T.

17. A device for monitoring according to claim 15, the magnetic resonance imaging system is adapted to apply a magnetic field whose magnetic field value comprised between 1.5 T and 3.0 T.

* * * * *